United States Patent
Meng et al.

(10) Patent No.: US 7,223,786 B2
(45) Date of Patent: May 29, 2007

(54) 2-AMINONAPHTHALENE DERIVATIVES AND RELATED GLYCOGEN PHOSPHORYLASE INHIBITORS

(75) Inventors: Wei Meng, Pennington, NJ (US); Philip M. Sher, Plainsboro, NJ (US); Bruce A. Ellsworth, Princeton, NJ (US); William N. Washburn, Titusville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/273,479

(22) Filed: Nov. 14, 2005

(65) Prior Publication Data

US 2006/0111415 A1 May 25, 2006

Related U.S. Application Data

(60) Provisional application No. 60/628,064, filed on Nov. 15, 2004.

(51) Int. Cl.
*A61K 31/405* (2006.01)
*C07D 209/12* (2006.01)
*C07D 209/14* (2006.01)

(52) U.S. Cl. ............ 514/419; 514/423; 548/492; 548/506; 548/510; 548/516

(58) Field of Classification Search ........ 514/419, 514/423; 548/492, 506, 510, 516
See application file for complete search history.

(56) References Cited

U.S. PATENT DOCUMENTS

| | | | |
|---|---|---|---|
| 5,952,322 A | 9/1999 | Hoover et al. | |
| 5,998,463 A | 12/1999 | Hulin et al. | |
| 6,589,970 B2 | 7/2003 | Commons et al. | |
| 6,660,742 B2 * | 12/2003 | Lee | 514/254.09 |
| 2001/0046958 A1 | 11/2001 | Treadway | |
| 2003/0073731 A1 | 4/2003 | Lee | |
| 2004/0002495 A1 | 1/2004 | Sher et al. | |

FOREIGN PATENT DOCUMENTS

| | | | |
|---|---|---|---|
| EP | 0 624 575 | 11/1994 | |
| EP | 978 279 | 2/2000 | |
| EP | 1 041 068 | 10/2000 | |
| EP | 1 149 580 | 1/2001 | |
| EP | 1 088 824 | 4/2001 | 495/4 |
| EP | 1 136 071 | 9/2001 | 31/0 |
| EP | 1 177 791 | 2/2002 | |
| JP | 9-100278 | 4/1997 | |
| JP | 2004-196702 | 7/2004 | |
| WO | WO 96/39384 | 12/1996 | |
| WO | WO 96/39385 | 12/1996 | |
| WO | WO 99/26659 | 6/1999 | |
| WO | WO 99/43663 | 9/1999 | |
| WO | WO 00/15645 | 3/2000 | |
| WO | WO 00/47206 | 8/2000 | |
| WO | WO 01/23347 | 4/2001 | |
| WO | WO 01/32622 | 5/2001 | |
| WO | WO 02/20530 | 3/2002 | |
| WO | WO 02/064546 | 8/2002 | |
| WO | WO 02/064565 | 8/2002 | |
| WO | WO 03/035621 | * 5/2003 | |
| WO | WO 03/037864 | 5/2003 | 209/42 |
| WO | WO 03/072570 | 9/2003 | 405/12 |
| WO | WO 03/074484 | 9/2003 | |
| WO | WO 03/074513 | 9/2003 | 401/12 |
| WO | WO 03/074531 | 9/2003 | |
| WO | WO 03/074532 | 9/2003 | 495/4 |
| WO | WO 03/091213 | 11/2003 | |
| WO | WO 03/104188 | 12/2003 | |
| WO | WO 04/041780 | 5/2004 | |
| WO | WO 04/072060 | 8/2004 | |
| WO | WO 04/078743 | 9/2004 | |

OTHER PUBLICATIONS

Proc. Natl. Acad. Sci. USA 1998, 95, 1776-1781.
J. Med. Chem. 1998, 41, 2934-2938.
Exp. Opin. Invest. Drugs 2001, 10, 439-454.
J. Med. Chem. 2002, 45, 1002-1018.
Journal of Pharmaceutical Sciences, vol. 64(6), 1975, 1001-1005.

* cited by examiner

*Primary Examiner*—Kamal A. Saeed
*Assistant Examiner*—Yong Chu
(74) *Attorney, Agent, or Firm*—Terence J. Bogie

(57) ABSTRACT

Novel compounds are provided which are glycogen phosphorylase inhibitors which are useful in treating, preventing or slowing the progression of diseases requiring glycogen phosphorylase inhibitor therapy such as diabetes and related conditions (such as hyperglycemia, impaired glucose tolerance, insulin resistance and hyperinsulinemia), the microvascular complications associated with diabetes (such as retinopathy, neuropathy, nephropathy and delayed wound healing), the macrovascular complications associated with diabetes (cardiovascular diseases such as atherosclerosis, abnormal heart function, myocardial ischemia and stroke), as well as Metabolic Syndrome and its component conditions including hypertension, obesity and dislipidemia (including hypertriglyceridemia, hypercholesterolemia and low HDL), and other maladies such as non-cardiac ischemia, infection and cancer. These novel compounds have the structure

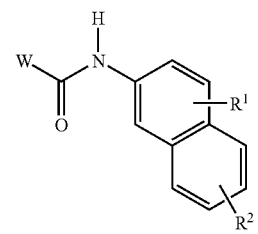

or stereoisomers or prodrugs or pharmaceutically acceptable salts thereof, wherein W, $R^1$ and $R^2$ are defined herein.

7 Claims, No Drawings

2-AMINONAPHTHALENE DERIVATIVES AND RELATED GLYCOGEN PHOSPHORYLASE INHIBITORS

This application claims the benefit of U.S. Provisional Application No. 60/628,064, filed Nov. 15, 2004, incorporated herein by reference in its entirety.

BACKGROUND OF THE INVENTION

Approximately 100 million people worldwide suffer from type II diabetes, which is typically characterized by hyperglycemia due to excessive hepatic glucose production and peripheral insulin resistance, the root causes for which are as yet unknown. Hyperglycemia is considered to be the major risk factor for the development of diabetic complications, such as retinopathy, neuropathy, nephropathy and macrovascular disease.

Accordingly, hepatic glucose production is an important potential target for type II diabetes therapy. The liver produces glucose by glycogenolysis (breakdown of the glucose polymer glycogen) and gluconeogenesis (synthesis of glucose from 2- and 3-carbon precursors). Particularly, glycogenolysis is catalyzed in the liver, muscle and brain by tissue-specific isoforms of the enzyme glycogen phosphorylase. Prior studies suggest that glycogenolysis may make an important contribution to hepatic glucose output in type II diabetes. See, for example, WO 96/39384; WO 96/39385; EP 978279; Proc. Natl. Acad. Sci. USA 1998, 95, 1776–1781; J. Med. Chem. 1998, 41, 2934–2938; Exp. Opin. Invest. Drugs 2001, 10, 439–454; EP 1136071; and WO 03/37864. Thus, glycogen phosphorylase inhibitors are believed to be useful therapeutic agents for treating type II diabetes and delaying the onset of diabetic complications by decreasing hepatic glucose production and lowering glycemia, while providing minimal risk of hypoglycemia and weight gain. See Id.

Based on the aforementioned references and additional references, for example, WO 96/39384; WO 96/39385; WO 00/47206; U.S. Pat. No. 5,952,322; WO 99/43663; EP 1088824; US 2001/0046958; EP 1149580; WO 01/23347; EP 1177791; WO 99/26659; U.S. Pat. No. 5,998,463; EP 1136071; US 2004/0002495 and EP 1041068, it is believed that glycogen phosphorylase inhibitors may be useful in treating, preventing or slowing the progression of diseases such as diabetes and related conditions (such as hyperglycemia, impaired glucose tolerance, insulin resistance and hyperinsulinemia), the microvascular complications associated with diabetes (such as retinopathy, neuropathy, nephropathy and delayed wound healing), the macrovascular complications associated with diabetes (cardiovascular diseases such as atherosclerosis, abnormal heart function, myocardial ischemia and stroke), as well as Metabolic Syndrome and its component conditions including hypertension, obesity and dislipidemia (including hypertriglyceridemia, hypercholesterolemia and low HDL), and other maladies such as non-cardiac ischemia, infection and cancer.

SUMMARY OF THE INVENTION

In accordance with the present invention, 2-aminonaphthalenes and related compounds are provided that have the general structure of formula I:

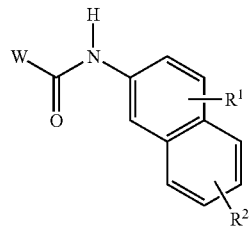

wherein W, $R^1$ and $R^2$ are defined below.

The compounds of the present invention inhibit the activity of the enzyme glycogen phosphorylase. Consequently, the compounds of the present invention may be used in the treatment of multiple diseases or disorders associated with glycogen phosphorylase activity, such as diabetes and related conditions (such as hyperglycemia, impaired glucose tolerance, insulin resistance and hyperinsulinemia), the microvascular complications associated with diabetes (such as retinopathy, neuropathy, nephropathy and delayed wound healing), the macrovascular complications associated with diabetes (cardiovascular diseases such as atherosclerosis, abnormal heart function, myocardial ischemia and stroke), as well as Metabolic Syndrome and its component conditions including hypertension, obesity and dislipidemia (including hypertriglyceridemia, hypercholesterolemia and low HDL), and other maladies such as non-cardiac ischemia, infection and cancer.

Inhibitors of the glycogen phosphorylase enzyme are also described in U.S. patent applications Ser. Nos. 11/273,167, 11/273,445 and 11/272,845, titled "2-Amino-3-Functionalized Tetralin Derivatives and Related Glycogen Phosphorylase Inhibitors", "2-Amino-1-Functionalized Tetralin Derivatives and Related Glycogen Phosphorylase Inhibitors" and "2-Amino-4-Functionalized Tetralin Derivatives and Related Glycogen Phosphorylase Inhibitors", respectively, having the same assignee as the present invention and filed concomitantly herewith.

The present invention provides for compounds of formula I, pharmaceutical compositions employing such compounds and for methods of using such compounds. In particular, the present invention provides a pharmaceutical composition comprising a therapeutically effective amount of a compound of formula I, alone or in combination with a pharmaceutically acceptable carrier.

Further, in accordance with the present invention, a method is provided for preventing, inhibiting or treating the progression or onset of diseases or disorders associated with the activity of the enzyme glycogen phosphorylase, such as defined above and hereinafter, wherein a therapeutically effective amount of a compound of formula I is administered to a mammalian, i.e., human, patient in need of treatment.

The compounds of the invention can be used alone, in combination with other compounds of the present invention, or in combination with one or more other agent(s).

Further, the present invention provides a method for preventing, inhibiting or treating the diseases as defined above and hereinafter, wherein a therapeutically effective amount of a combination of a compound of formula I and another compound of formula I and/or at least one other type of therapeutic agent, is administered to a mammalian, i.e., human, patient in need of treatment.

DETAILED DESCRIPTION OF THE INVENTION

In one embodiment, the present invention discloses novel compounds of formula I:

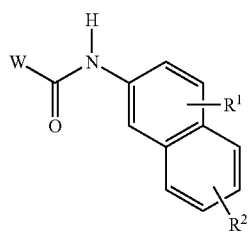

I or stereoisomers or prodrugs or pharmaceutically acceptable salts thereof, wherein:

W is a bicyclic heteroaryl of the structure

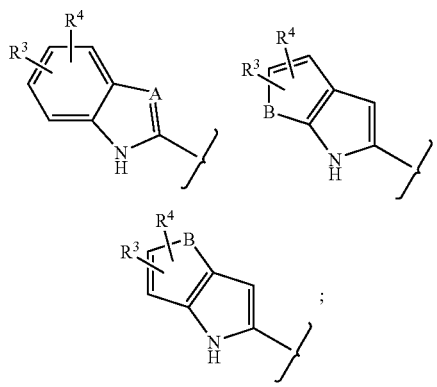

;

A is —CH— or —N—;
B is —O— or —S—;
$R^1$, which may attach at any of the three positions of the WCONH-bearing ring of the naphthalene ring system, is independently hydrogen, alkyl, aryl, arylalkyl, heteroarylalkyl, alkenyl, $OR^{5A}$, $OCO_2R^6$, $OCONR^{5A}R^{5B}$, CN, $CN_4R^{5A}$ (tetrazole), $CO_2R^{5A}$, $CONR^{5A}R^{5B}$, $CONR^{5A}OR^{5B}$, $NR^{5A}COCO_2R^{5B}$ or another hydrogen bonding group;
$R^2$, which may attach at any of the four positions on the non-WCONH-bearing ring of the naphthalene ring system, is independently hydrogen, halo, trifluoromethyl, cyano, hydroxy, another hydrogen bonding group, alkyl, aryl, arylalkyl, heteroarylalkyl, alkoxy, aryloxy or alkenyl;
$R^3$ and $R^4$ are each independently hydrogen, halo, trifluoromethyl, cyano, alkyl or alkoxy; and
$R^{5A}$ and $R^{5B}$ are independently hydrogen, alkyl, arylalkyl, heteroarylalkyl or aryl, or $R^{5A}$ and $R^{5B}$ may optionally be cyclized together to form a ring, wherein said ring may further be substituted with one to three additional hydrogen bonding groups; and
$R^6$ is alkyl, aryl, arylalkyl or heteroarylalkyl;

wherein when $R^1$ and $R^2$ are alkyl, aryl, arylalkyl, heteroarylalkyl, alkenyl, alkoxy or aryloxy, $R^1$ and $R^2$ may each independently be substituted with one to three hydrogen bonding groups.

Some preferred compounds are those in which W is:

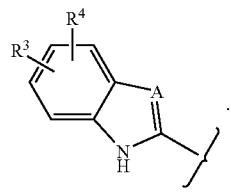

Some more preferred compounds are those in which A is —CH—.
Some even more preferred compounds are those in which $R^1$ is independently substituted alkyl, $OR^{5A}$, $OCONR^{5A}R^{5B}$, CN, $CN_4R^{5A}$ (tetrazole), $CO_2R^{5A}$, $CONR^{5A}R^{5B}$ or $NR^{5A}COCO_2R^{5B}$;
$R^2$ and $R^3$ are hydrogen;
$R^4$ is halo, trifluoromethyl or cyano; and
$R^{5A}$ and $R^{5B}$ are hydrogen or alkyl.
Some additional preferred compounds of the present invention are those in which:
the hydrogen bonding group is preferably selected from the set of monovalent hydrogen bonding groups consisting of $OR^{5A}$, $OCO_2R^6$, $OCONR^{5A}R^{5B}$, CN, $NO_2$, $CN_4R^{5A}$ (tetrazole), $COCF_3$, $COR^{5A}$, $CO_2R^{5A}$, $CONR^{5A}R^{5B}$, $CONR^{5A}OR^{5B}$, $C(NR^{5A})NR^{5B}R^{5C}$, $CONR^{5A}SO_2R^{5B}$, $SOR^6$, $SO_2R^6$, $SO_3H$, $SO_2NR^{5A}R^{5B}$, $SO_2NR^{5A}COR^{5B}$, $SO_2NR^{5A}CONR^{5B}R^{5C}$, $POR^{5A}R^{5B}$, $PO_2R^{5A}R^{5B}$, $PO_3R^{5A}R^{5B}$, $PO_2R^{5A}NR^{5B}R^{5C}$, $NR^{5A}R^{5B}$, $NR^{5A}COR^{5B}$, $NR^{5A}C(NR^{5B})R^{5C}$, $NR^{5A}CO_2R^6$, $NR^{5A}COCO_2R^{5B}$, $NR^{5A}CONR^{5B}R^{5C}$, $NR^{5A}C(NR^{5B})NR^{5C}R^{5D}$, $NR^{5A}SO_2R^{5B}$, $NR^{5A}CONR^{5B}SO_2R^{5C}$, $NR^{5A}SO_2NR^{5B}R^{5C}$, $NR^{5A}POR^{5B}R^{5C}$, $NR^{5A}PO_2R^{5B}R^{5C}$, $NR^{5A}PO_3R^{5B}R^{5C}$ and $NR^{5A}PO_2R^{5B}NR^{5C}R^{5D}$, or the set of divalent hydrogen bonding groups consisting of —O—, —CO—, —SO_2—, —NR^{5A}—, —CO_2—, —CONR^{5A}—, —SO_2NR^{5A}—, —OCONR^{5A}—, —NR^{5A}CONR^{5B}—, —N(COR^{5A})—, —N(CO_2R^{5A})—, —N(CONR^{5A}R^{5B})— and —N(SO_2NR^{5A}R^{5B})—;
wherein
$R^{5C}$ and $R^{5D}$ are each independently hydrogen, alkyl, arylalkyl, heteroarylalkyl or aryl; and wherein $R^{5A}$, $R^{5B}$, $R^{5C}$, $R^{5D}$ or $R^6$ may further be substituted with one to three additional hydrogen bonding groups; and
wherein
two of $R^{5A}$, $R^{5B}$, $R^{5C}$ or $R^{5D}$ within the same hydrogen bonding group may optionally be cyclized together to form a ring, wherein said ring may further be substituted with one to three additional hydrogen bonding groups.
Preferred compounds also include those compounds in which:
W is

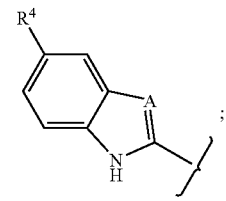

;

A is —CH—; and
$R^4$ is halo, trifluoromethyl or cyano.

Some particularly preferred compounds are those in which W is 5-chloroindol-2-yl.

Some more particularly preferred compounds are those in which the compound is selected from the compounds of Table 1.

In another embodiment, the present invention relates to pharmaceutical compositions comprised of a therapeutically effective amount of a compound of the present invention, alone or, optionally, in combination with a pharmaceutically acceptable carrier and/or one or more other agent(s).

In another embodiment, the present invention relates to methods of inhibiting the activity of the enzyme glycogen phosphorylase comprising administering to a mammalian patient, preferably a human patient, in need thereof a therapeutically effective amount of a compound of the present invention, alone, or optionally, in combination with another compound of the present invention and/or at least one other type of therapeutic agent.

In another embodiment, the present invention relates to a method for preventing, inhibiting or treating the progression or onset of diseases or disorders associated with the activity of the enzyme glycogen phosphorylase comprising administering to a mammalian patient, preferably a human patient, in need of prevention, inhibition or treatment a therapeutically effective amount of a compound of the present invention, alone, or, optionally, in combination with another compound of the present invention and/or at least one other type of therapeutic agent.

Examples of diseases or disorders associated with the activity of the enzyme glycogen phosphorylase that can be prevented, inhibited, or treated according to the present invention include, but are not limited to, diabetes and related conditions (such as hyperglycemia, impaired glucose tolerance, insulin resistance and hyperinsulinemia), the microvascular complications associated with diabetes (such as retinopathy, neuropathy, nephropathy and delayed wound healing), the macrovascular complications associated with diabetes (cardiovascular diseases such as atherosclerosis, abnormal heart function, myocardial ischemia and stroke), as well as Metabolic Syndrome and its component conditions including hypertension, obesity and dislipidemia (including hypertriglyceridemia, hypercholesterolemia and low HDL), and other maladies such as non-cardiac ischemia, infection and cancer.

DEFINITIONS

The following abbreviations have the indicated meanings:
min=minute(s)
h or hr=hour(s)
L=liter(s)
mL=milliliter(s)
μL=microliter(s)
g=gram(s)
mg milligram(s)
mol mole(s)
M=molar
mmol=millimole(s)
HPLC=high performance liquid chromatography
HPLC/MS or LC/MS=high performance liquid chromatography/mass spectrometry
MS or Mass Spec=mass spectrometry
[M+H]$^+$=parent plus a proton
[M−H]$^−$=parent minus a proton The following definitions apply to the terms as used throughout this specification, unless otherwise limited in specific instances.

The term "hydrogen bonding group(s)" describes functional groups that may form a hydrogen bond by either donating or accepting a hydrogen atom. Examples of suitable "hydrogen bonding group(s)" include, but are not limited to the monovalent groups $OR^{5A}$, $OCO_2R^6$, $OCONR^{5A}R^{5B}$, $CN$, $NO_2$, $CN_4R^{5A}$ (tetrazole), $COCF_3$, $COR^{5A}$, $CO_2R^{5A}$, $CONR^{5A}R^{5B}$, $CONR^{5A}OR^{5B}$, $C(NR^{5A})NR^{5B}R^{5C}$, $CONR^{5A}SO_2R^{5B}$, $SOR^6$, $SO_2R^6$, $SO_3H$, $SO_2NR^{5A}R^{5B}$, $SO_2NR^{5A}COR^{5B}$, $SO_2NR^{5A}CONR^{5B}R^{5C}$, $POR^{5A}R^{5B}$, $PO_2R^{5A}R^{5B}$, $PO_3R^{5A}R^{5B}$, $PO_2R^{5A}NR^{5B}R^{5C}$, $NR^{5A}R^{5B}$, $NR^{5A}COR^{5B}$, $NR^{5A}C(NR^{5B})R^{5C}$, $NR^{5A}CO_2R^6$, $NR^{5A}COCO_2R^{5B}$, $NR^{5A}CONR^{5B}R^{5C}$, $NR^{5A}C(NR^{5B})NR^{5C}R^{5D}$, $NR^{5A}SO_2R^{5B}$, $NR^{5A}CONR^{5B}SO_2R^{5C}$, $NR^{5A}SO_2NR^{5B}R^{5C}$, $NR^{5A}POR^{5B}R^{5C}$, $NR^{5A}PO_2R^{5B}R^{5C}$, $NR^{5A}PO_3R^{5B}R^{5C}$ and $NR^{5A}PO_2R^{5B}NR^{5C}R^{5D}$, and the divalent groups —O—, —CO—, —SO$_2$—, —NR$^{5A}$—, —CO$_2$—, —CONR$^{5A}$—, —SO$_2$NR$^{5A}$—, —OCONR$^{5A}$—, —NR$^{5A}$CONR$^{5B}$—, —N(COR$^{5A}$)—, —N(CO$_2$R$^{5A}$)—, —N(CONR$^{5A}$R$^{5B}$)— and —N(SO$_2$NR$^{5A}$R$^{5B}$)—, and the like, wherein $R^{5A}$, $R^{5B}$, $R^{5C}$ and $R^{5D}$ for each occurrence are each independently hydrogen, alkyl, arylalkyl, heteroarylalkyl or aryl; and $R^6$ is alkyl, arylalkyl, heteroarylalkyl, or aryl.

Moreover, $R^{5A-5D}$ and $R^6$ may be further substituted with one to three hydrogen bonding groups. For example, by substitution with the monovalent hydrogen bonding group OH, $CONR^{5A}R^{5B}$ may represent $CON(Me)CH_2CH_2OH$. Optionally, two of $R^{5A}$, $R^{5B}$, $R^{5C}$ or $R^{5D}$ within the same hydrogen bonding group may be cyclized together to form a ring by joining the two R groups with either a bond or with a divalent hydrogen bonding group. For example, $CONR^{5A}R^{5B}$ may represent $CON(CH_2CH_2CH_2CH_2)$, N-acylated pyrrolidine, or $CON(CH_2CH_2NHCH_2CH_2)$, N-acylated piperidine. Said ring may further be substituted with one to three additional hydrogen bonding groups, for example N-acylated hydroxyproline or N-acylated 3,4-dihydroxypyrrolidine.

In addition, when an R group is itself equal to a hydrogen bonding group, said hydrogen bonding group is a monovalent hydrogen bonding group. However, when an R group is substituted with a hydrogen bonding group, said hydrogen bonding group may be either a monovalent or a divalent hydrogen bonding group.

Substitution of any single R group with a divalent hydrogen bonding group preferably forms a ring. For example, substitution of a 2-butyl group at the 1- and 4-positions with —O— forms a 3-tetrahydrofuranyl group. Substitution of a 1-pentyl group at the 1- and 5-positions with —CO— forms a 2-oxocyclohexyl group.

The term "alkyl" as employed herein, alone or as part of another group, includes straight chain, branched chain and saturated cyclic hydrocarbons, containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, cyclopropyl, cyclohexyl, and the like.

Unless otherwise indicated, the term "alkenyl" as used herein by itself or as part of another group refers to straight or branched chain radicals of 2 to 20 carbons, preferably 2 to 12 carbons, and more preferably 2 to 8 carbons in the normal chain, that include one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl.

Unless otherwise indicated, the term "aryl" or "Ar" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one additional fused heterocyclic ring, for example:

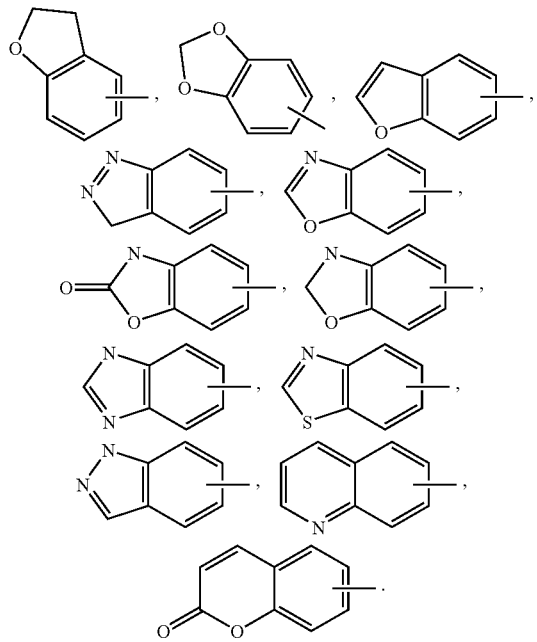

Aryl groups as defined above may optionally be substituted with alkyl groups containing up to six carbons and/or with halogen groups.

The term "arylalkyl" as used alone or as part of another group refers to an alkyl as defined herein, having an aryl substituent. Representative examples of arylalkyl include, but are not limited to, benzyl, 2-phenylethyl, 3-phenylpropyl, benzhydryl, naphthylmethyl, 4-trifluoromethylphenylpropyl and the like.

The term "halogen" or "halo" as used herein alone or as part of another group refers to chlorine, bromine, fluorine and iodine and also to pseudohalogen groups such as trifluoromethyl, trifluoromethoxy and difluoromethoxy.

Unless otherwise indicated, the term "alkoxy" or "aryloxy" as employed herein alone or as part of another group refers to an alkyl or aryl group, as defined herein, linked to an oxygen atom.

Unless otherwise indicated, the term "heteroaryl" as used herein alone or as part of another group refers to a 5- or 6-membered aromatic ring which includes 1, 2, 3 or 4 heteroatoms such as nitrogen, oxygen or sulfur, and includes possible N-oxides. Examples of heteroaryl groups include the following:

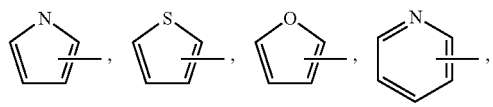

-continued

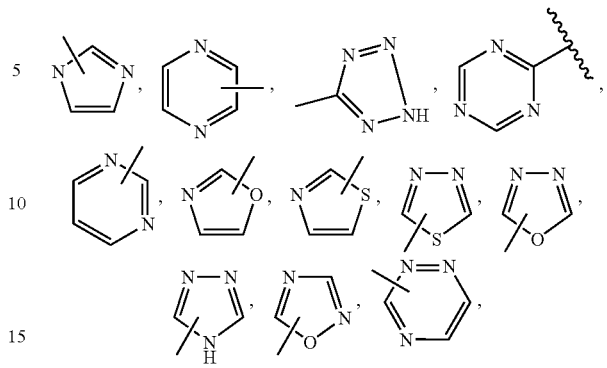

and the like.

Heteroaryl groups as defined above may optionally be substituted with alkyl groups containing up to six carbons and/or with halogen groups.

As used herein, the term "heteroarylalkyl" means an alkyl group having a heteroaryl substituent.

The term "cyano" as used herein, refers to a —CN group.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$–$C_4$) alkyl or arylsulfonic acids which are unsubstituted or substituted, for example by halogen, for example methyl- or p-toluenesulfonic acid. Corresponding acid addition salts can also be formed having, if desired, an additionally present basic center. The compounds of formula I having at least one acid group (for example COOH) can form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl, tert-butyl, diethyl, diisopropyl, triethyl, tributyl or dimethylpropylamine, or a mono-, di- or trihydroxy lower alkylamine, for example mono-, di- or triethanolamine. Corresponding internal salts may furthermore be formed. Salts which are unsuitable for pharmaceutical uses but which can be employed, for example, for the isolation or purification of free compounds of formula I or their pharmaceutically acceptable salts, are also included.

Preferred salts of the compounds of formula I which contain a basic group include monohydrochloride, hydrogensulfate, methanesulfonate, phosphate or nitrate salts.

Preferred salts of the compounds of formula I which contain an acid group include sodium, potassium and magnesium salts and pharmaceutically acceptable organic amine salts.

Any compound that can be converted in vivo to provide the bioactive agent (i.e., the compound of formula I) is a prodrug within the scope and spirit of the invention.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like.

Various forms of prodrugs are well known in the art and are described in:

a) *The Practice of Medicinal Chemistry*, Camille G. Wermuth et al., Ch. 31, (Academic Press, 1996);
b) *Design of Prodrugs*, edited by H. Bundgaard, (Elsevier, 1985);
c) *A Textbook of Drug Design and Development*, P. Krogsgaard-Larson and H. Bundgaard, eds. Ch. 5, pgs 113–191 (Harwood Academic Publishers, 1991); and
d) *Hydrolysis in Drug and Prodrug Metabolism*, Bernard Testa and Joachim M. Mayer, (Wiley-VCH, 2003).

Said references are incorporated herein by reference.

In addition, compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All stereoisomers and polymorphs of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of formula I can exist in enantiomeric, diastereomeric, or polymorphic forms or in mixtures thereof. The processes for preparation can utilize racemates, enantiomers, diastereomers or polymorphs as starting materials. When diastereomeric or enantiomeric products are prepared, they can be separated by conventional methods for example, chromatographic or fractional crystallization.

SYNTHESIS

The compounds of formula I of the invention can be prepared as shown below in the following reaction schemes and description thereof, as well as by using relevant published literature procedures that may be used by one skilled in the art. Exemplary reagents and procedures for these reactions appear hereinafter and in the working Examples.

Compounds of formula I may be prepared by coupling carboxylic acids of formula II with amines of formula III using standard methods for amide bond formation, as known to those skilled in the art, for example, by treating equimolar amounts of compounds II and III in N,N-dimethylformamide solution at room temperature with equimolar amounts of 1-hydroxy-7-azabenzotriazole and 1-[3-dimethylamino)propyl]-3-ethylcarbodiimide hydrochloride.

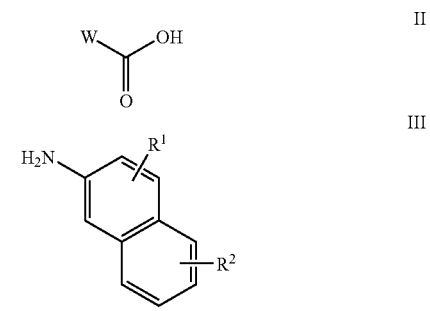

Carboxylic acids II may be prepared according to the routes and procedures described in WO 9639384, WO 9926659, and EP 1088824.

Amines III may be prepared by deprotection of the corresponding protected amines IV, in which the amino group is protected (PGN) as a carbamate, amide, phthalimide, N-benzyl derivative, or other standard amine protecting group, such as described in Protective Groups in Organic Synthesis (2$^{nd}$ Edition, T. W. Greene and P. G. M. Wuts, John Wiley & Sons, 1991).

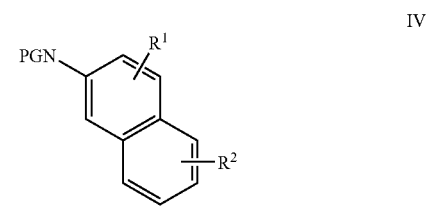

Also included in the definition of protected amine IV are compounds in which the amino group is masked (PGN), i.e., the latent amino group may not fall into the strict definition of a protecting group, such as an azido or nitro group. Protected amines IV wherein the amino group is masked as a carbamate, amide, phthalimide, N-benzyl derivative, or other standard amine protecting group may be prepared from the amines III as described in Protective Groups in Organic Synthesis. A reason for converting an amine III to a protected amine IV would be to modify $R^1$ and/or $R^2$ prior to deprotection to regenerate a different amine III. Azido, nitro, and some protected amino groups, such as benzylamino, may be introduced by other means, such as displacement (azido and benzylamino). Carbamates may be prepared not only from the corresponding amine, but also from carboxylic acids by Curtius rearrangement, via the acid chloride, acyl azide and isocyanate (see Comprehensive Organic Synthesis, Editor B. M. Trost, Pergamon Press, 1991).

A number of especially useful amines III are commercially available or known in the literature as shown in Chart I.

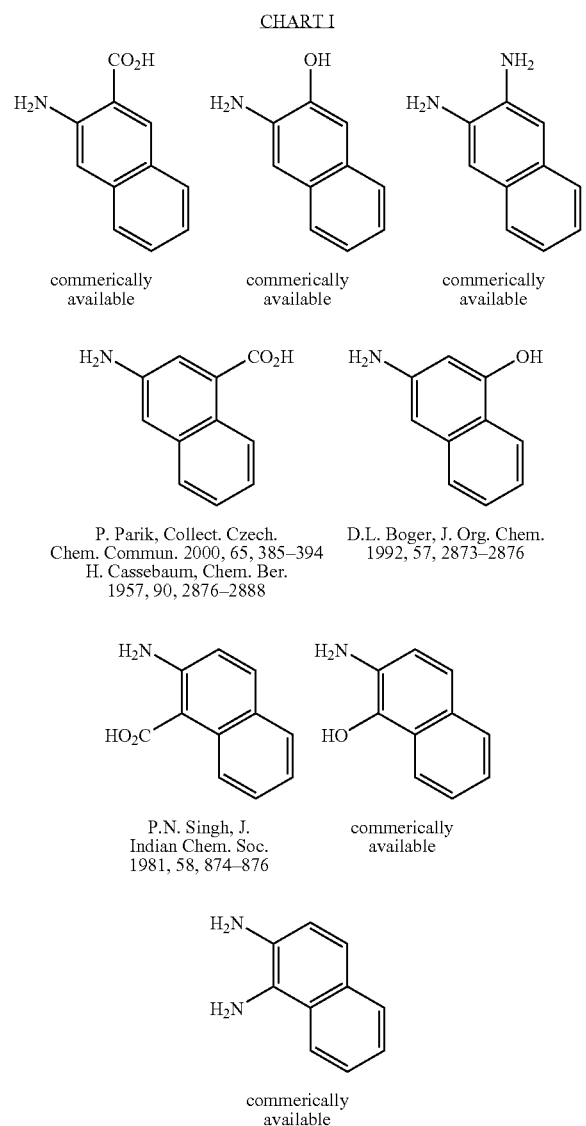

CHART I

Additionally, the book The Chemistry and Technology of Naphthalene Compounds (N. Donaldson, Edward Arnold Publishers, 1958) provides naphthalene compound-specific synthetic information, particularly in chapters VII and XI, which discuss naphthylamines substituted with halo, nitro and hydroxyl groups. Another useful reference work for naphthalene compound chemistry is volume III of Rodd's Chemistry of Carbon Compounds, Editor S. Coffey, Elsevier Publishing Company, 1971.

In general, the interchange of functional groups within $R^1$ and $R^2$, including the formation of various hydrogen bonding groups, may be accomplished according to the methods and procedures described in Compendium of Organic Synthetic Methods (John Wiley & Sons), Comprehensive Organic Functional Group Transformations (Editors A. R. Katritzky, O. Meth-Cohn and C. W. Rees, Pergamon Press) and Comprehensive Organic Transformations—A Guide To Functional Group Preparations (R. C. Larock, VCH Publishers, 1989). For example, a protected amine IV in which $R^1$ is 2-hydroxyethylaminocarbonyl may be prepared from the corresponding compound in which $R^1$ is a carboxyl group by standard amide coupling chemistry using 2-hydroxyethylamine. As another example, a protected amine IV in which $R^1$ is an acylated amino group such as carboxycarbonylamino may be prepared from the corresponding compound in which $R^1$ is a carboxyl group by Curtius rearrangement followed by acylation with methyl oxalyl chloride and ester hydrolysis with sodium hydroxide. It is understood that during the course of manipulating any functional group within $R^1$ and $R^2$, standard protecting groups, as described in Protective Groups in Organic Synthesis, may be employed to avoid undesired reaction of any other functional group, or of the indole ring or other bicyclic heterocycle W, particularly at its nitrogen, or of the amide linking W to the rest of the molecule.

Standard protecting groups may be used at any stage of the synthesis, for example in manipulating a functional group to convert one compound of formula I to another compound of formula I, or in manipulating a functional group to convert one protected amine IV to another protected amine IV, or to avoid undesired reaction during the coupling of carboxylic acid II and amine III, or during the sequence of steps leading to the formation of either carboxylic acid II or protected amine IV.

As known to those skilled in the art, most functional group transformation chemistry that is effective for interconverting substituents attached to an isolated benzene ring is also effective for interconverting substituents on a naphthalene ring. Therefore, the general references Compendium of Organic Synthetic Methods, Comprehensive Organic Functional Group Transformations and Comprehensive Organic Transformations—A Guide To Functional Group Preparations provide adequate information for one skilled in the art to effect interconversions of functional groups within $R^1$ and $R^2$. Accordingly, in Comprehensive Organic Transformations—A Guide To Functional Group Preparations by Larock the transformation index keyword "arene" is used to search the chemistry of transformations of functional groups attached to either isolated benzene rings or naphthalene ring systems.

Table B below highlights some of the standard aromatic ring substituent functional group manipulations known to those skilled in the art that are potentially useful for introduction or manipulation of $R^1$ or $R^2$ or the reactive amino group in amines III. In certain entries the Desired Product Functional Group is marked with an asterisk (*). In these cases the functional group is introduced ortho to a pre-existing functional group such as PGN. Most of the references are attributed to Larock with the page number on which the method appears in Comprehensive Organic Transformations—A Guide To Functional Group Preparations. In Table B, LG represents a leaving group, especially chloride, bromide, iodide, methanesulfonate and trifluoromethanesulfonate, which is useful in nucleophilic displacement and palladium catalyzed coupling reactions. The group M represents a monovalent metal atom or group that renders nucleophilic the group to which it is attached. For example M may be lithium as in butyl lithium, chloromagnesium as in benzylmagnesium chloride, etc. The group R (lacking a superscripted numeral) represents an alkyl or benzyl group.

TABLE B

ArX → ArY

| Desired Product Group Y | Starting Material Group X | Reagents | Reference |
|---|---|---|---|
| OH | $NH_2$ | $NaNO_2$, $H_2SO_4$ b. $H_2O$, heat | Larock 483 |
| OH | OR | HBr, AcOH | Larock 501 |
| OH | LG | a. BuLi b. $(Me_3SiO)_2$ | Larock 490 |
| OH | $COCH_3$ | mCPBA b. NaOH | Larock 843 |
| $CO_2H$* | H | a. RLi b. $CO_2$ | Larock 50 |
| $CO_2H$ | LG | CO, ROH, Pd cat. b. NaOH | Larock 855, 856 |
| $CO_2H$ | $CH_3$ | $KMnO_4$ | Larock 823 |
| $CO_2H$ | CN | HCl, $H_2O$ | Larock 993 |
| $CO_2H$ | $COCH_3$ | $I_2$, NaOH | Larock 842 |
| $NH_2$ | $CO_2H$ | $SOCl_2$ b. $NaN_3$ c. $H_2O$, heat | Larock 431 |
| $NH_2$ | $NO_2$ | $H_2$, cat. | Larock 412 |
| $NH_2$ | LG | RLi b. $H_2NOMe$ | Larock 399 |
| LG | H | $Br_2$ | Larock 315 |
| LG* | H | a. RLi b. $I_2$ | Larock 50 |
| LG | OH | $Tf_2O$, pyr | |
| OR | LG | NaOR, Pd cat. | Mann and Palucki |
| $COCH_3$ | H | $Ac_2O$, Lewis acid | Larock 703 |
| CN | LG | CuCN | Larock 861 |
| $NO_2$ | H | $HNO_3$, $H_2SO_4$ | |
| $CH_2NH_2$ | CN | $BH_3$ | Larock 437 |

Schemes 1–5 set forth below are provided as non-limiting illustrations of the breadth of possible synthetic manipulations. Scheme 1 illustrates $R^1$ manipulation. Scheme 2 illustrates $R^2$ manipulation. Scheme 3 illustrates $R^1$ and $R^2$ manipulation. Scheme 4 illustrates amino group installation. Scheme 5 illustrates amino group installation and $R^1$ manipulation. For transformations that Table B does not address, standard reagents are included.

SCHEME 1

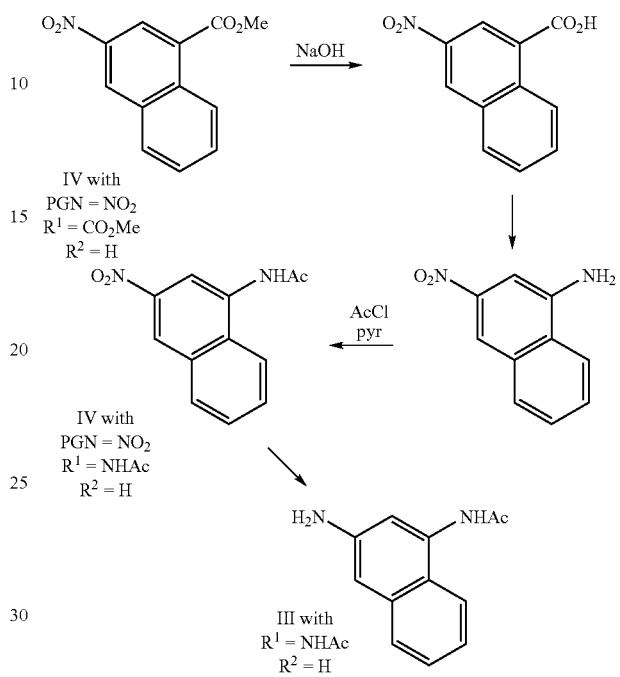

SCHEME 2

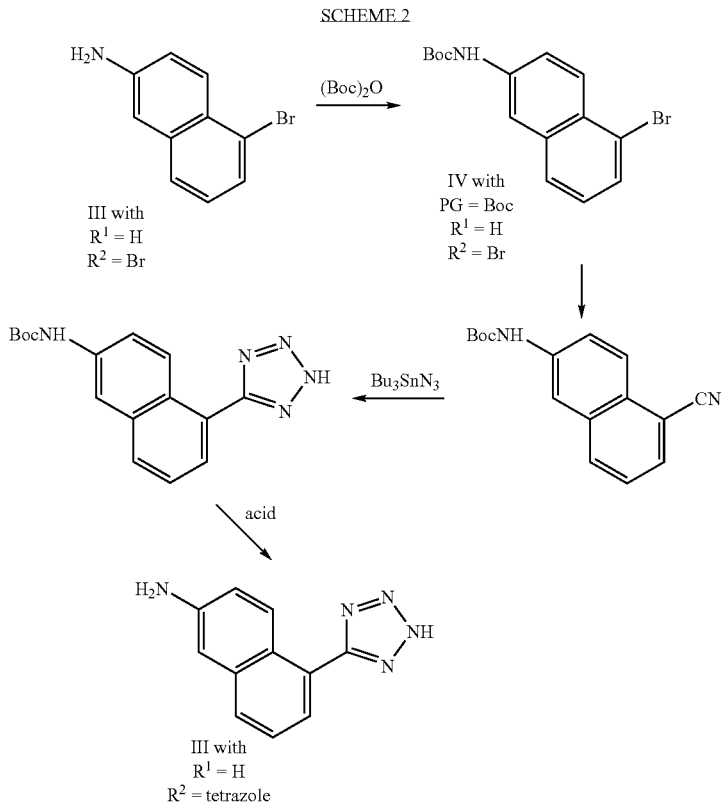

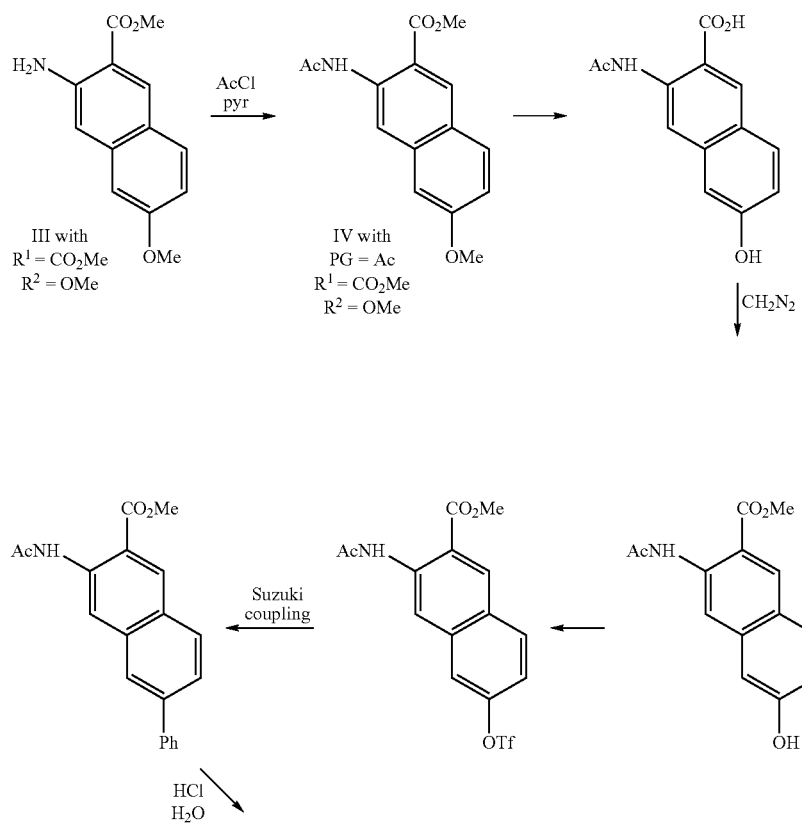
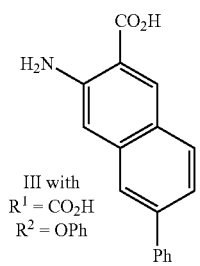
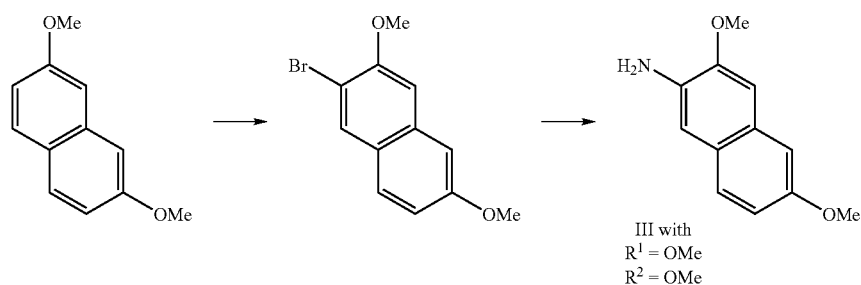

SCHEME 5

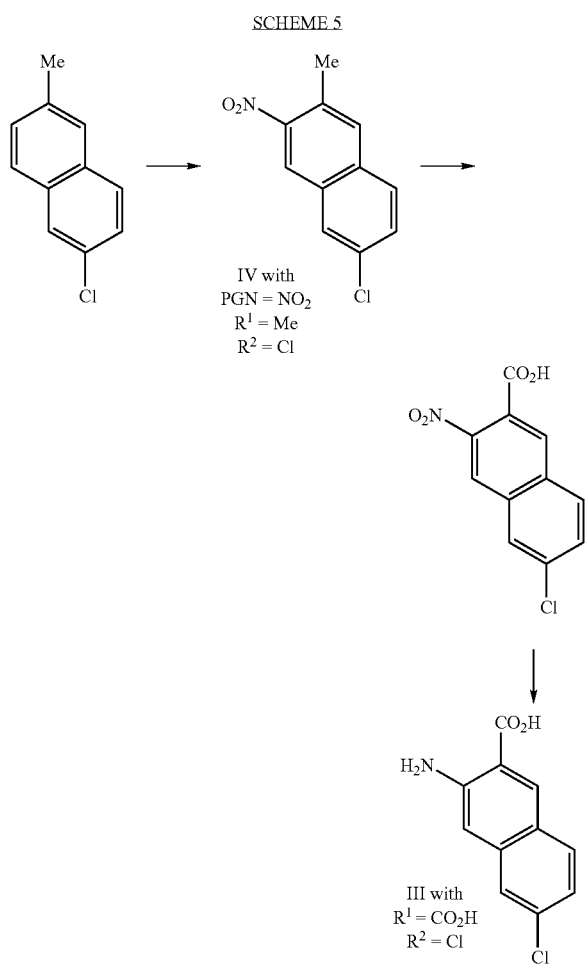

In the synthetic schemes set forth above, the reagent lists are abbreviated. References cited above provide full details and in some cases alternative reagents. It is understood that the reagents shown in the synthetic schemes are example reagents, not meant to be limiting. Those skilled in the art will recognize that there are many acids (hydrochloric acid, polyphosphoric acid, etc.), many bases (sodium hydride, potassium methoxide, etc.), many oxidants (hydrogen peroxide, 3-chloroperoxybenzoic acid, Dess-Martin periodinane, etc.), many hydrogenation catalysts (palladium, platinum oxide, Raney® Nickel, etc.), and so on that may be employed to synthesize the compounds of the invention. In some cases alternative reagents known to those skilled in the art will be superior to those listed in the synthetic schemes. Alternative reagents may be found in Reagents For Organic Synthesis (Fieser and Fieser, John Wiley & Sons) and Compendium of Organic Synthetic Methods (John Wiley & Sons). These references will also provide guidance in cases where the synthetic schemes designate only a class of reagent rather than a specific reagent (for example oxidant rather than hydrogen peroxide). In some instances the synthetic schemes refer not to specific reagents or reagent classes, but rather to name reactions, for example Suzuki coupling. These name reactions and their experimental details are well-known to those skilled in the art (see Organic Syntheses Based on Name Reactions and Unnamed Reactions, A. Hassner and C. Stumer, Pergamon Press, 1994).

The references provided are not intended to constrain the applicability of the reaction steps, but rather to exemplify the reactions and provide further experimental detail. The references are designated by either a patent/publication number or the first author of a scientific journal publication. Full scientific journal publication references according to first author are as follows: Mann, J. Org. Chem. 1997, 62, 5413–5418; Palucki, J. Am. Chem. Soc. 1997, 119, 3395–3396.

In the spirit of further illustration of the manipulation of functional groups within $R^1$ and $R^2$, compounds of formula I and protected amines IV wherein $R^1$ or $R^2$ is cyano, alkyl, aryl, arylalkyl, heteroarylalkyl, alkoxy, aryloxy or alkenyl may be prepared from compounds of formula I and protected amines IV wherein $R^1$ or $R^2$ is halo or hydroxy, using various palladium catalyzed coupling procedures as described in Aranyos, et al., J. Am. Chem. Soc. 1999, 121, 4369–4378 and Hamann, et al., J. Am. Chem. Soc. 1998, 120, 7369–7370 and references contained therein, and in recent papers authored by Gregory C. Fu, Stephen L. Buchwald, or John F. Hartwig. These procedures are directly applicable when $R^1$ or $R^2$ is halo. When $R^1$ or $R^2$ is hydroxy, prior activation by conversion of the hydroxyl group to a trifluoromethylsulfonyloxy group, as described in the aforementioned references, is required.

Compounds of formula I and protected amines IV in which $R^1$ is $OR^{5A}$, $OCO_2R^6$ or $OCONR^{5A}R^{5B}$, or wherein $R^2$ is substituted or unsubstituted alkoxy or aryloxy, may be prepared by elaboration of the analogous compounds of formula I and protected amines IV wherein $R^1$ or $R^2$, respectively, is hydroxy. For instance, a compound wherein $R^1$ is benzyloxy may be prepared by benzylation of the compound wherein $R^1$ is hydroxy with benzyl bromide. A compound wherein $R^2$ is carbomethoxymethoxy may be prepared from the compound in which $R^2$ is hydroxy by alkylation with methyl bromoacetate. A compound wherein $R^2$ is carboxymethoxy may be prepared by hydrolysis of the compound wherein $R^2$ is carbomethoxymethoxy or carbo-t-butyloxymethoxy. A compound wherein $R^2$ is 2-hydroxyethoxy may be prepared by reduction of the compound wherein $R^2$ is carbomethoxymethoxy or carboxymethoxy. A compound wherein $R^2$ is 2,3-dihydroxypropyloxy may be prepared from the compound wherein $R^2$ is hydroxy by alkylation with glycidyl 3-nitrobenzenesulfonate, followed by epoxide hydrolysis. A compound wherein $R^2$ is aryloxy may be prepared from the compound in which $R^2$ is hydroxy and an aryl halide by various palladium catalyzed coupling procedures as described in Aranyos, et al., J. Am. Chem. Soc. 1999, 121, 4369–4378 and references contained therein, and in recent papers authored by Stephen L. Buchwald.

The references above are incorporated herein by reference.

UTILITIES AND COMBINATIONS

A. Utilities

The compounds of the present invention possess activity as inhibitors of the enzyme glycogen phosphorylase and therefore may be used in the treatment of diseases associated with glycogen phosphorylase activity. Via the inhibition of glycogen phosphorylase, the compounds of the present invention may preferably be employed to inhibit glycogenolysis, thereby interrupting or modulating hepatic glucose production.

Accordingly, the compounds of the present invention can be administered to mammals, preferably humans, for the treatment of a variety of conditions and disorders, including, but not limited to, treating, preventing or slowing the progression of diabetes and related conditions (such as hyperglycemia, impaired glucose tolerance, insulin resistance and hyperinsulinemia), the microvascular complications associated with diabetes (such as retinopathy, neuropathy, nephropathy and delayed wound healing), the macrovascular complications associated with diabetes (cardiovascular diseases such as atherosclerosis, abnormal heart function, myocardial ischemia and stroke), as well as Metabolic Syndrome and its component conditions including hypertension, obesity and dislipidemia (including hypertriglyceridemia, hypercholesterolemia and low HDL), and other maladies such as non-cardiac ischemia, infection and cancer.

Metabolic Syndrome or "Syndrome X" is described in Ford, et al., *J. Am. Med. Assoc.* 2002, 287, 356–359 and Arbeeny, et al., *Curr. Med. Chem.—Imm., Endoc. & Metab. Agents* 2001, 1, 1–24.

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may employed in combination with other glycogen phosphorylase inhibitors or one or more other suitable therapeutic agents useful in the treatment of the aforementioned disorders including: antidiabetic agents; anti-atherosclerotic agents; anti-ischemic agents; anti-infective agents; anti-cancer and cytotoxic agents; anti-hyperglycemic agents; lipid lowering agents; anti-hypertensive agents; anti-obesity agents and appetite suppressants.

Examples of suitable anti-diabetic agents for use in combination with the compounds of the present invention include insulin and insulin analogs: LysPro insulin, inhaled formulations comprising insulin; glucagon-like peptides; sulfonylureas and analogs: chlorpropamide, glibenclamide, tolbutamide, tolazamide, acetohexamide, glypizide, glyburide, glimepiride, repaglinide, meglitinide; biguanides: metformin, phenformin, buformin; alpha2-antagonists and imidazolines: midaglizole, isaglidole, deriglidole, idazoxan, efaroxan, fluparoxan; other insulin secretagogues: linogliride, insulinotropin, exendin-4, BTS-67582, A-4166; thiazolidinediones: ciglitazone, pioglitazone, troglitazone, rosiglitazone; PPAR-gamma agonists; PPAR-alpha agonists; PPAR alpha/gamma dual agonists; SGLT2 inhibitors; dipeptidyl peptidase-IV (DPP4) inhibitors; aldose reductase inhibitors; RXR agonists: JTT-501, MCC-555, MX-6054, DRF2593, GI-262570, KRP-297, LG100268; fatty acid oxidation inhibitors: clomoxir, etomoxir, α-glucosidase inhibitors: precose, acarbose, miglitol, emiglitate, voglibose, MDL-25,637, camiglibose, MDL-73,945; beta-agonists: BRL 35135, BRL 37344, Ro 16-8714, ICI D7114, CL 316,243, TAK-667, AZ40140; phosphodiesterase inhibitors, both cAMP and cGMP type: sildenafil, L686398: L-386, 398; amylin antagonists: pramlintide, AC-137; lipoxygenase inhibitors: masoprocal; somatostatin analogs: BM-23014, seglitide, octreotide; glucagon antagonists: BAY 276-9955; insulin signaling agonists, insulin mimetics, PTP1B inhibitors: L-783281, TER17411, TER17529; gluconeogenesis inhibitors: GP3034; somatostatin analogs and antagonists; antilipolytic agents: nicotinic acid, acipimox, WAG 994; glucose transport stimulating agents: BM-130795; glucose synthase kinase inhibitors: lithium chloride, CT98014, CT98023 and galanin receptor agonists.

Other suitable thiazolidinediones include Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi).

Suitable PPAR alpha/gamma dual agonists include AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation—Activated Receptor Alpha (PPAR alpha) and PPAR gamma; Effect of PPAR alpha Activation on Abnormal Lipid Metabolism in Liver of Zucker Fatty Rats", Diabetes 47, 1841–1847 (1998), and WO 01/21602, the disclosure of which is incorporated herein by reference, employing dosages as set out therein, which compounds designated as preferred are preferred for use herein.

Suitable alpha2 antagonists also include those disclosed in WO 00/59506, employing dosages as set out herein.

Suitable SGLT2 inhibitors include T-1095, phlorizin, WAY-123783 and those described in WO 01/27128.

Suitable DPP4 inhibitors include those disclosed in WO99/38501, WO99/46272, WO99/67279 (PROBIO-DRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) as disclosed by Hughes et al, Biochemistry, 38 (36), 11597–11603, 1999, TSL-225 (tryptophyl-1,2,3,4-tetrahydroisoquinoline-3-carboxylic acid (disclosed by Yamada et al, Bioorg. & Med. Chem. Lett. 8 (1998) 1537–1540, 2-cyanopyrrolidides and 4-cyanopyrrolidides, as disclosed by Ashworth et al, Bioorg. & Med. Chem. Lett., Vol. 6, No. 22, pp 1163–1166 and 2745–2748 (1996) employing dosages as set out in the above references.

Suitable aldose reductase inhibitors include those disclosed in WO 99/26659.

Suitable meglitinides include nateglinide (Novartis) or KAD1229 (PF/Kissei).

Examples of glucagon-like peptide-1 (GLP-1) include GLP-1 -(1–36) amide, GLP-1 (7–36) amide, GLP-1 (7–37) (as disclosed in U.S. Pat. No. 5,614,492 to Habener), as well as AC2993 (Amylen) and LY-315902 (Lilly).

Other anti-diabetic agents that can be used in combination with compounds of the invention include ergoset and D-chiroinositol.

Suitable anti-ischemic agents include, but are not limited to, those described in the Physicians' Desk Reference and NHE inhibitors, including those disclosed in WO 99/43663.

Examples of suitable anti-infective agents are antibiotic agents, including, but not limited to, those described in the Physicians' Desk Reference.

Examples of suitable lipid lowering agents for use in combination with the compounds of the present invention include one or more MTP inhibitors, HMG CoA reductase inhibitors, squalene synthetase inhibitors, fibric acid derivatives, ACAT inhibitors, lipoxygenase inhibitors, cholesterol absorption inhibitors, ileal Na⁺/bile acid cotransporter inhibitors, upregulators of LDL receptor activity, bile acid sequestrants, cholesterol ester transfer protein inhibitors (e.g., CP-529414 (Pfizer)) and/or nicotinic acid and derivatives thereof.

MTP inhibitors which may be employed as described above include those disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. Pat. No. 5,962,440.

The HMG CoA reductase inhibitors which may be employed in combination with one or more compounds of formula I include mevastatin and related compounds, as disclosed in U.S. Pat. No. 3,983,140, lovastatin (mevinolin) and related compounds, as disclosed in U.S. Pat. No. 4,231,938, pravastatin and related compounds, such as disclosed in U.S. Pat. No. 4,346,227, simvastatin and related compounds, as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin, as disclosed in U.S. Pat. Nos. 5,006,530 and 5,177,080, atorvastatin, as disclosed in U.S. Pat. Nos. 4,681,893, 5,273,995, 5,385,929 and 5,686,104, atavastatin (Nissan/Sankyo's nisvastatin (NK-104)), as disclosed in U.S. Pat. No. 5,011,930, visastatin (Shionogi-Astra/Zeneca (ZD-4522)), as disclosed in U.S. Pat. No. 5,260,440, and related statin compounds disclosed in U.S. Pat. No. 5,753,675, pyrazole analogs of mevalonolactone derivatives, as disclosed in U.S. Pat. No. 4,613,610, indene analogs of mevalonolactone derivatives, as disclosed in PCT application WO 86/03488, 6-[2-(substituted-pyrrol-1-yl)alkyl)pyran-2-ones and derivatives thereof, as disclosed in U.S. Pat. No. 4,647,576, Searle's SC-45355 (a 3-substituted pentanedioic acid derivative) dichloroacetate, imidazole analogs of mevalonolactone, as disclosed in PCT application WO 86/07054, 3-carboxy-2-hydroxy-propane-phosphonic acid derivatives, as disclosed in French Patent No. 2,596,393, 2,3-disubstituted pyrrole, furan and thiophene derivatives, as disclosed in European Patent Application No. 0221025, naphthyl analogs of mevalonolactone, as disclosed in U.S. Pat. No. 4,686,237, octahydronaphthalenes, such as disclosed in U.S. Pat. No. 4,499,289, keto analogs of mevinolin (lovastatin), as disclosed in European Patent Application No. 0142146 A2, and quinoline and pyridine derivatives, as disclosed in U.S. Pat. Nos. 5,506,219 and 5,691,322.

Preferred hypolipidemic agents are pravastatin, lovastatin, simvastatin, atorvastatin, fluvastatin, cerivastatin, atavastatin and ZD-4522.

In addition, phosphinic acid compounds useful in inhibiting HMG CoA reductase, such as those disclosed in GB 2205837, are suitable for use in combination with the compounds of the present invention.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869–1871, including isoprenoid (phosphinyl-methyl)phosphonates, as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1–40 (1996).

In addition, other squalene synthetase inhibitors suitable for use herein include the terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98, 1291–1293, phosphinylphosphonates reported by McClard, R. W. et al, J.A.C.S., 1987, 109, 5544 and cyclopropanes reported by Capson, T. L., Ph.D. dissertation, June, 1987, Dept. Med. Chem. U of Utah, Abstract, Table of Contents, pp. 16, 17, 40–43, 48–51, Summary.

The fibric acid derivatives which may be employed in combination with one or more compounds of formula I include fenofibrate, gemfibrozil, clofibrate, bezafibrate, ciprofibrate, clinofibrate and the like, probucol, and related compounds, as disclosed in U.S. Pat. No. 3,674,836, probucol and gemfibrozil being preferred, bile acid sequestrants, such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents.

The ACAT inhibitor which may be employed in combination with one or more compounds of formula I include those disclosed in Drugs of the Future 24, 9–15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137(1), 77–85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359–62, or TS-962 (Taisho Pharmaceutical Co. Ltd.).

The hypolipidemic agent may be an upregulator of LD2 receptor activity, such as MD-700 (Taisho Pharmaceutical Co. Ltd) and LY295427 (Eli Lilly).

Examples of suitable cholesterol absorption inhibitor for use in combination with the compounds of the invention include SCH48461 (Schering-Plough), as well as those disclosed in Atherosclerosis 115, 45–63 (1995) and J. Med. Chem. 41, 973 (1998).

Examples of suitable ileal Na+/bile acid cotransporter inhibitors for use in combination with the compounds of the invention include compounds as disclosed in Drugs of the Future, 24, 425–430 (1999).

The lipoxygenase inhibitors which may be employed in combination with one or more compounds of formula I include 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199–1206, and Comicelli et al, "15-Lipoxygenase and its Inhibition: A Novel Therapeutic Target for Vascular Disease", Current Pharmaceutical Design, 1999, 5, 11–20.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetamide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-obesity agents for use in combination with the compounds of the present invention include a cannabinoid receptor 1 antagonist or inverse agonist, a beta 3 adrenergic agonist, a lipase inhibitor, a serotonin (and dopamine) reuptake inhibitor, a thyroid receptor beta drug and/or an anorectic agent.

Cannabinoid receptor 1 antagonists and inverse agonists which may be optionally employed in combination with compounds of the present invention include rimonabant, SLV 319 and those discussed in D. L. Hertzog, Expert Opin. Ther. Patents 2004, 14, 1435–1452.

The beta 3 adrenergic agonists which may be optionally employed in combination with compounds of the present invention include AJ9677 (Takeda/Dainippon), L750355 (Merck), or CP331648 (Pfizer,) or other known beta 3 agonists, as disclosed in U.S. Pat. Nos. 5,541,204, 5,770,615, 5,491,134, 5,776,983 and 5,488,064, with AJ9677, L750,355 and CP331648 being preferred.

Examples of lipase inhibitors which may be optionally employed in combination with compounds of the present invention include orlistat or ATL-962 (Alizyme), with orlistat being preferred.

The serotonin (and dopamine) reuptake inhibitor which may be optionally employed in combination with a compound of formula I may be sibutramine, topiramate (Johnson & Johnson) or axokine (Regeneron), with sibutramine and topiramate being preferred.

Examples of thyroid receptor beta compounds which may be optionally employed in combination with compounds of the present invention include thyroid receptor ligands, such as those disclosed in WO97/21993 (U. Cal SF) and WO99/00353 (KaroBio), with compounds of the KaroBio applications being preferred.

The anorectic agent which may be optionally employed in combination with compounds of the present invention include dexamphetamine, phentermine, phenylpropanolamine or mazindol, with dexamphetamine being preferred.

Other compounds that can be used in combination with the compounds of the present invention include CCK receptor agonists (e.g., SR-27895B); galanin receptor antagonists; MCR-4 antagonists (e.g., HP-228); leptin or mimentics; 11-beta-hydroxysteroid dehydrogenase type-1 inhibitors; urocortin mimetics, CRF antagonists, and CRF binding proteins (e.g., RU-486, urocortin).

Further, the compounds of the present invention may be used in combination with anti-cancer and cytotoxic agents, including but not limited to alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, mitomycin, dactinomycin, and plicamycin; enzymes such as L-asparaginase; farnesyl-protein transferase inhibitors; 5α reductase inhibitors; inhibitors of 17β-hydroxy steroid dehydrogenase type 3; hormonal agents such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel (Taxol®), docetaxel (Taxotere®), and their analogs, and epothilones, such as epothilones A-F and their analogs; plant-derived products, such as vinca alkaloids, epipodophyllotoxins, taxanes; and topiosomerase inhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators and monoclonal antibodies. Additional anti-cancer agents are disclosed in EP 1177791. The compounds of the invention may also be used in conjunction with radiation therapy.

The aforementioned patents and patent applications are incorporated herein by reference.

The above other therapeutic agents, when employed in combination with the compounds of the present invention may be used, for example, in those amounts indicated in the Physician's Desk Reference, as in the patents set out above or as otherwise determined by one of ordinary skill in the art.

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intrastemal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

In carrying out the method of the invention for treating diabetes and related diseases, a pharmaceutical composition will be employed containing the compounds of formula I, with or without other antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders and the like. The compounds can be administered to a mammalian patient, including humans, monkeys, dogs, etc. by an oral route, for example, in the form of tablets, capsules, beads, granules or powders. Typical solid formulations will contain from about 1 to about 1000 mg of a compound of formula I. The dose for adults is preferably between 1 and 2,000 mg per day, which can be administered in a single dose or in the form of individual doses from 1–4 times per day.

It will be understood that the specific dose level and frequency of dosage for any particular subject can be varied and will depend upon a variety of factors including the potency of the specific compound employed, the metabolic stability and length of action of that compound, the species, age, body weight, general health, sex and diet of the subject, the mode and time of administration, rate of excretion, drug combination, and severity of the particular condition.

Glycogen phosphorylase inhibitor activity of the compounds of the invention may be determined by use of an assay system as set out below.

ASSAY FOR GLYCOGEN PHOSPHORYLASE ACTIVITY

The utility of the compounds of the invention for use in the treatment of diabetes and the other conditions that may be treated with a glycogen phosphorylase inhibitor may be demonstrated in assays for glycogen phosphorylase inhibition in vitro (U.S. Pat. No. 6,107,329), effects on blood sugar and insulin in vivo (U.S. Pat. No. 6,107,329), effects on ischemic tissue damage in vitro (U.S. Pat. No. 6,107,329), and effects on weight and food intake in vivo (WO 00/47206). Compounds deemed herein to possess activity as inhibitors of the enzyme glycogen phosphorylase demonstrate an $IC_{50}$ of 10 μM or lower when measured in the aforementioned glycogen phosphorylase inhibition in vitro assay.

EXAMPLES

The following working Examples serve to better illustrate, but not limit, some of the preferred embodiments of the present invention.

General

Reverse phase preparative HPLC separation employed an octadecyl sulfate (C-18) column eluting with a solvent gradient of solvents A and B, starting with 20% or more of solvent B and finishing with 100% of solvent B. Solvent A was 10% methanol in water, and solvent B was 90% methanol in water. In many cases both solvents A and B contained 0.1% of trifluoroacetic acid, as noted. Reverse phase analytical HPLC employed the same type of column and solvents, except that the solvents contained 0.2% phosphoric acid.

For Examples 1 to 4 see Table 1:

TABLE 1

| Example | $R^1$ |
|---------|-------|
| 1 | OH |
| 2 | $CO_2H$ |
| 3 | $CONMe_2$ |
| 4 | $NHCOCO_2H$ |

Example 1

5-Chloro-1H-indole-2-carboxylic acid (3-hydroxynaphthalen-2-yl)amide

To a stirred solution of 5-chloroindole-2-carboxylic acid (86 mg, 0.44 mmol) in tetrahydrofuran (2 mL) at room temperature under nitrogen was added oxalyl chloride (2.0 M in dichloromethane solution, 0.45 mL, 0.90 mmol) and N,N-dimethylformamide (0.010 mL). After 1 h, the reaction mixture was concentrated under vacuum to provide the acid chloride, which was taken up in tetrahydrofuran (3 mL). To the resulting solution stirring under nitrogen at room temperature was added 3-amino-2-naphthol (70 mg, 0.44 mmol) followed by triethylamine (0.3 mL, 2.2 mmol). After 1 h, the reaction mixture was quenched by addition of 1.0 M aqueous hydrochloric acid solution and diluted with ethyl acetate. The reaction mixture was filtered to remove insoluble materials. The filtrate was washed sequentially with 1.0 M aqueous hydrochloric acid solution and brine, dried over anhydrous magnesium sulfate, and concentration under vacuum to yield a residue. The residue was suspended in methanol and the methanol solution phase was purified by reverse phase preparative HPLC (trifluoroacetic acid containing solvents were used) to obtain Example 1 (16 mg, 11%) as a light yellow solid. $^1$H NMR (400 MHz, $d_8$-tetrahydrofuran) δ 9.61 (s, 1H), 9.13 (s, 1H), 8.79 (s, 1H), 7.74 (d, J=7.0 Hz, 1H), 7.66 (s, 1H), 7.61 (d, J=7.6 Hz, 1H), 7.45 (d, J=7.2 Hz, 1H), 7.19 (m, 4H), 7.17 (s, 1H), 7.13 (s, 1H). MS $[M+H]^+$, 337; $[M-H]^-$, 335.

Example 2

3-[(5-Chloro-1H-indole-2-carbonyl)amino]naphthalene-2-carboxylic acid

To a stirred solution of 5-chloroindole-2-carboxylic acid (300 mg, 1.53 mmol) in tetrahydrofuran (10 mL) at room temperature under nitrogen was added oxalyl chloride (2.0 M in dichloromethane solution, 1.53 mL, 3.06 mmol) and N,N-dimethylformamide (0.010 mL). After 1.5 h, the reaction mixture was concentrated under vacuum to yield the acid chloride. The acid chloride was dissolved in tetrahydrofuran (10 mL) stirring under nitrogen at room temperature, and 3-amino-2-naphthoic acid (287 mg, 1.53 mmol) was added followed by triethylamine (1.1 mL, 7.7 mmol). After 2 h, the reaction mixture was quenched by addition of 1.0 M aqueous hydrochloric acid solution and diluted with ethyl acetate. The organic layer was washed sequentially with 1.0 M aqueous hydrochloric acid solution, saturated aqueous sodium bicarbonate solution, saturated aqueous ammonium chloride solution and brine, dried over anhydrous magnesium sulfate, and concentrated under vacuum to yield a residue. The residue was suspended in methanol and filtered to collect Example 2 (300 mg, 54%) as a light yellow solid. $^1$H NMR (500 MHz, d$_8$-tetrahydrofuran) δ 12.42 (s, 1H), 11.38 (s, 1H), 9.33 (s, 1H), 8.79 (s, 1H), 7.91 (d, J=7.5 Hz, 1H), 7.87 (d, J=7.5 Hz, 1H), 7.68 (s, 1H), 7.57 (t, J=6.6 Hz, 1H), 7.45 (m, 2H), 7.21 (d, J=6.5 Hz, 1H), 7.13 (s, 1H). HPLC/MS [M+H]$^+$, 365; [M−H]$^−$, 363.

Example 3

5-Chloro-1H-indole-2-carboxylic acid (3-dimethylcarbamoylnaphthalen-2-yl)amide

To a stirred solution of Example 2 (45 mg, 0.12 mmol) in tetrahydrofuran (3 mL) at room temperature under nitrogen was added oxalyl chloride (2.0 M in dichloromethane solution, 0.12 mL, 0.24 mmol) and N,N-dimethylformamide (0.010 mL). After 1 h, the reaction mixture was concentrated under vacuum to yield the acid chloride. The acid chloride was dissolved in tetrahydrofuran (3 mL) stirring under nitrogen at room temperature, and N,N-dimethylformamide (1.5 mL) and dimethylamine hydrochloride (20 mg, 0.24 mmol), 1-[3-dimethylamino)propyl]-3-ethylcarbodiimide hydrochloride (47 mg, 0.24 mmol), 1-hydroxy-7-azabenzotriazole (33 mg, 0.24 mmol) and diisopropylethylamine (0.2 mL, 1.2 mmol) were added. The reaction mixture was stirred for 16 h before dilution with ethyl acetate. The organic layer was washed sequentially with 1.0 M aqueous hydrochloric acid solution, 1.0 M aqueous sodium hydroxide solution and brine, dried over anhydrous magnesium sulfate, and concentrated under vacuum to yield a residue. The residue was suspended in methanol and filtered to collect Example 3 (39 mg, 81%) as a light yellow solid. $^1$H NMR (400 MHz, d$_8$-tetrahydrofuran) δ 12.02 (s, 1H), 10.50 (s, 1H), 8.22 (s, 1H), 8.00 (s, 1H), 7.97 (t, J=7.5 Hz, 1H), 7.79 (s, 1H), 7.55 (m, 2H), 7.47 (d, J=7.8 Hz, 1H), 7.24 (m, 3H), 3.03 (s, 3H), 3.00 (s, 3H). MS [M+H]$^+$, 392; [M−H]$^−$, 390.

Example 4

N-{3-[(5-Chloro-1H-indole-2-carbonyl)amino]naphthalen-2-yl}oxalamic acid

Part I: 2-Amino-3-(5-chloroindole-2-carbonylamino)naphthalene

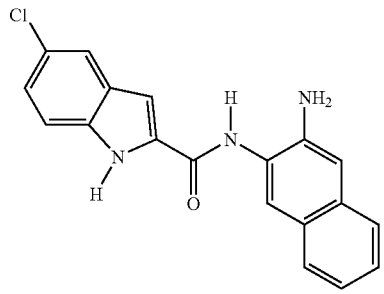

A solution of 5-chloroindole-2-carboxylic acid (247 mg), 2,3-diaminonaphthalene (200 mg), 1-hydroxybenzotriazole hydrate (221 mg), 1-[3-dimethylamino)propyl]-3-ethylcarbodiimide hydrochloride (315 mg) and triethylamine (447 mg) in N,N-dimethylformamide was stirred under nitrogen at room temperature for 3 h. The reaction mixture was diluted with water before extraction with ethyl acetate (three times). The combined organic extracts were washed sequentially with saturated aqueous ammonium chloride solution, water and saturated aqueous sodium bicarbonate solution (three times each), dried over anhydrous magnesium sulfate and evaporated under vacuum to yield a solid. The solid was triturated with chloroform and then dried under vacuum to obtain the title compound as a tan solid (102 mg).

Part II: N-{3-[(5-Chloro-1H-indole-2-carbonyl)amino]naphthalen-2-yl}oxalamic acid ethyl ester

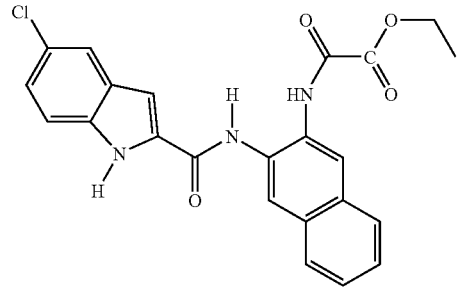

To a solution of 2-amino-3-(5-chloroindole-2-carbonylamino)naphthalene (50 mg) in tetrahydrofuran (<1 mL) stirring at room temperature under argon, was added ethyl oxalyl chloride (40 mg) followed by triethylamine (34 mg). After 2 h, the reaction mixture was diluted with water and then extracted with ethyl acetate (three times). The combined organic extracts were dried over anhydrous magnesium sulfate and evaporated under vacuum to yield a residue. The residue was subjected to silica gel chromatography eluted with 30% ethyl acetate in hexane to obtain the title compound.

Part III: Example 4

To a solution of N-{3-[(5-chloro-1H-indole-2-carbonyl)amino]naphthalen-2-yl}oxalamic acid ethyl ester (15 mg) in methanol and tetrahydrofuran (1:1, 0.4 mL), stirring at room temperature, was added 1.0 M aqueous sodium hydroxide solution (0.04 mL). After 2 h, 1.0 M aqueous hydrochloric acid solution was added to acidify to pH 2–3, and the mixture was purified directly by reverse phase preparative HPLC (trifluoroacetic acid containing solvents were used) to obtain Example 4 as a yellow solid. HPLC/MS [M+H]$^+$, 408.

Example 5

3-[(5-Chloro-1H-indole-2-carbonyl)amino]naphthalene-1-carboxylic acid

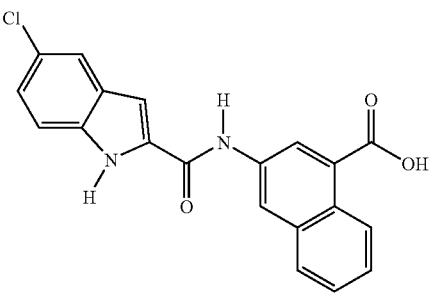

To a stirring solution of 5-chloroindole-2-carboxylic acid (0.20 g) in tetrahydrofuran (1.5 mL) at room temperature under argon was added oxalyl chloride (2.0 M in dichloromethane, 0.5 mL), followed by N,N-dimethylformamide (1 drop). The solution bubbled for 10 min. After 2 h, a small sample of the solution was quenched with methanol and then analyzed by HPLC/MS, which indicated that at least 75% of the acid had been converted to acid chloride (based on observation of both the acid chloride itself and its methyl ester). In a separate reaction vessel, 3-amino-1-carboxynaphthalene hydrochloride (prepared in the manner described in P. Parik, Collect. Czech. Chem. Commun. 2000, 65, 385–394, 0.24 g) was slurried in tetrahydrofuran (5 mL) at room temperature under argon. The resulting mixture was stirred as diisopropylethylamine (0.74 g) was added. A poorly soluble gum formed. To this gum was added the solution of acid chloride prepared above. The gum was dissolved and a solid precipitate slowly formed. The resulting mixture was analyzed by HPLC/MS, which indicated the formation of both desired product and bisacylation product in a 1:1 ratio. Tetrahydrofuran (10 mL) was added, and the resulting mixture (pH 11) was refluxed for 1 h. After this time, the mixture was again analyzed by HPLC/MS, which indicated the ratio of desired product to bisacylation product was 7:1. The mixture was cooled room temperature. Once at room temperature, 1.0 M aqueous hydrochloric acid solution (6 µL) and water (35 mL) were added to achieve a pH of 1, and stirring was discontinued. Some solid and oil formed and settled. The supernatant was removed and discarded. The solid and oil were stirred with water, which caused the oil to solidify. Again, the supernatant was removed and discarded. The solid was briefly boiled in methanol, and after cooling to room temperature, the supernatant extract was collected. This methanol extraction procedure was repeated (3 times), and the combined extracts were purified by reverse phase preparative HPLC (trifluoroacetic acid containing solvents were used) to obtain Example 5 (109 mg) as a solid. HPLC/MS [M+H]$^+$, 365; [M–H]$^-$, 363.

What is claimed is:

1. A compound of the formula I

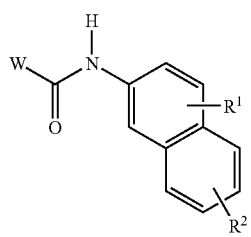

or stereoisomers or prodrugs or pharmaceutically acceptable salts thereof, wherein:

W is a bicyclic heteroaryl of the structure

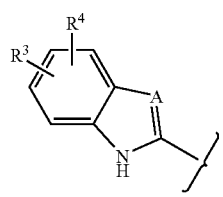

A is —CH—;

$R^1$ is independently substituted alkyl, $OR^{5A}$, $OCONR^{5A}R^{5B}$, CN, tetrazole substituted $R^{5A}$, $CO_2R^{5A}$, $CONR^{5A}R^{5B}$ or $NR^{5A}COCO_2R^{5B}$;

$R^2$ and $R^3$ are hydrogen;

$R^4$ is halo, trifluoromethyl or cyano; and $R^{5A}$ and $R^{5B}$ are hydrogen or alkyl.

2. A compound selected from the group consisting of:

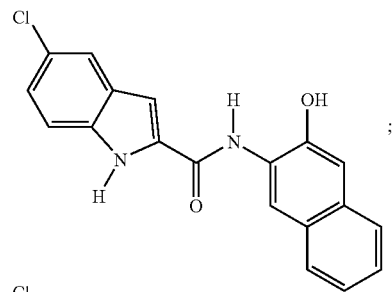

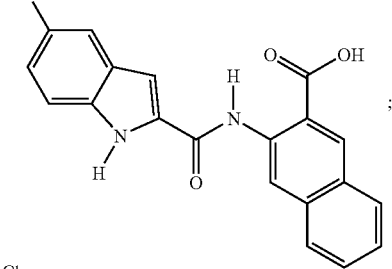

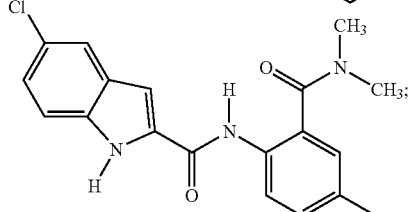

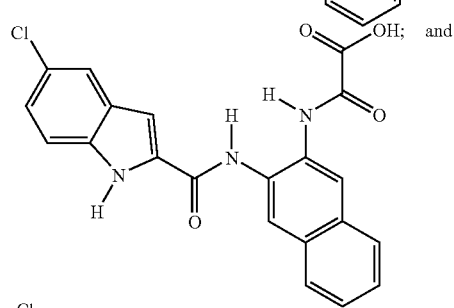

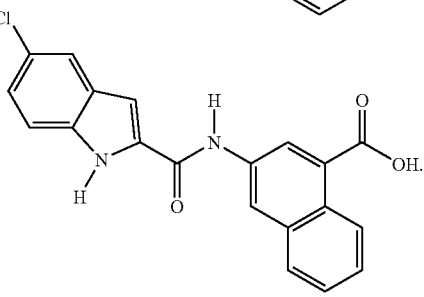

3. A pharmaceutical composition comprised of a compound of claim 2 and a pharmaceutically acceptable carrier.

4. The compound of claim 1 wherein W is 5-chloroindol-2-yl.

5. The pharmaceutical composition of claim 3 further comprising one or more other therapeutic agents.

6. A pharmaceutical composition comprising a compound of claim 1 and a pharmaceutically acceptable carrier.

7. The pharmaceutical composition of claim 6 further comprising one or more other therapeutic agents.

* * * * *